United States Patent [19]

Ballard et al.

[11] Patent Number: 5,866,418
[45] Date of Patent: Feb. 2, 1999

[54] MILK PROTEIN MIXTURE FOR PROMOTING GROWTH OF ANIMAL CELLS OR TREATING WOUNDS AND METHOD OF MAKING AND METHODS EMPLOYING THE MIXTURE

[75] Inventors: Francis John Ballard, Glenalta; Geoffrey Leonard Francis, Athelstone; Geoffrey Owen Regester, Collinswood, all of Australia

[73] Assignee: Gropep Pty. Ltd., South Australia, Australia

[21] Appl. No.: 956,759

[22] PCT Filed: Jul. 9, 1991

[86] PCT No.: PCT/AU91/00303

§ 371 Date: Dec. 7, 1992

§ 102(e) Date: Dec. 7, 1992

[87] PCT Pub. No.: WO92/00994

PCT Pub. Date: Jul. 9, 1991

[30] Foreign Application Priority Data

Jul. 13, 1990 [AU] Australia .................. PK1170

[51] Int. Cl.⁶ ..................................................... C12N 5/06
[52] U.S. Cl. .................. 435/384; 435/325; 424/535; 530/350; 530/399; 530/416
[58] Field of Search ................................ 435/252.1, 253, 435/240.1, 240.2, 240.3, 325, 384; 424/535; 530/399, 350, 416

[56] References Cited

U.S. PATENT DOCUMENTS

| | | | |
|---|---|---|---|
| 3,967,337 | 7/1976 | Lauer | 260/112 B |
| 3,969,337 | 7/1976 | Lauer | 260/112 R |
| 4,440,860 | 4/1984 | Klagsbrun | 435/240 |
| 4,668,771 | 5/1987 | Kawakami et al. | 530/366 |
| 4,783,524 | 11/1988 | Larsen et al. | 530/350 |
| 4,791,193 | 12/1988 | Okonogi et al. | 530/416 |
| 5,055,558 | 10/1991 | Chiancone et al. | 530/386 |
| 5,221,734 | 6/1993 | Burk et al. | 530/399 |
| 5,500,229 | 3/1996 | Aalto et al. | 424/535 |

FOREIGN PATENT DOCUMENTS

| | | |
|---|---|---|
| 67992/74 | 10/1975 | Australia . |
| 83720/82 | 11/1982 | Australia . |
| 52480/86 | 2/1985 | Australia . |
| 49227/85 | 7/1986 | Australia . |
| 23326/88 | 1/1989 | Australia . |
| 2332688 | 1/1989 | Australia . |
| 0219372 | 4/1987 | European Pat. Off. . |
| 253395 | 1/1988 | European Pat. Off. . |
| 285576 | 10/1988 | European Pat. Off. . |
| 313515 | 4/1989 | European Pat. Off. . |
| 59-166879 | 9/1984 | Japan . |
| 59-166897 | 9/1984 | Japan . |
| 1507790 | 9/1989 | U.S.S.R. . |
| WO 90/06357 | 6/1990 | WIPO . |

OTHER PUBLICATIONS

*Tissue Growth Factors*, ed. by R. Baserga, chapt. 8 pp. 247–276 (1981).

Gaull et al *Pediatrics* 75(1, part 2) 1985 pp 142–145 Significance of Growth Modulator . . .

Damerdji et al., "Utilization of Whey Fractions as a Substitute for Fetal Calf Serum in Culture Media", *Biotech. Tech.*, 2:235 (1988).

Klagsbrun, "Human Milk Stimulates DNA Synthesis and Cell Proliferation in Cultured Fibroblasts", *Proc. Natl. Acad. Sci. USA*, 75:5057 (1978).

Klagsbrun et al., "The Serum–Free Growth of Balb/c 3T3 Cells in Medium Supplemented with Bovine Colostrum", *J. Supremol. Struct.*, 11:349 (1979).

Oliver et al., "A Rapid and Convenient Assay for Counting Cells Cultured inMicrowell Plates: Application for Assessment of Growth Factors", *J. Cell Biol.*, 92:513 (1989).

Cox, David A. and Burk, Robert R., Isolation and characterisation of milk growth factor, a transforming–growth factor–β2–related polypeptide, from bovine milk, Eur. J. Biochem. 197:353–358 (1991).

Van Brunt et al., Biotehcnology 6(1):25–30 (Jan. 1988).

*Primary Examiner*—Chhaya D. Sayala
*Attorney, Agent, or Firm*—Merchant, Gould, Smith, Edell, Welter & Schmidt, P.A.

[57] ABSTRACT

The present invention relates to a milk protein mixture useful for promoting growth of animal cells, for treating a surface wound, or for treating a gastrointestinal injury, disease, or ulcer, methods for preparing the milk protein mixture and methods employing the milk protein mixture. The milk protein mixture is prepared from a milk product such as cheese whey employing a cation exchange resin suitable for absorbing the milk protein mixture, filtering, and concentrating the product of cation exchange. The milk protein mixture for promoting growth of animal cells also includes a liquid culture medium. The milk protein mixture for treating a surface wound or for treating a gastrointestinal injury, disease, or ulcer also includes a pharmaceutically or veterinarily acceptable diluent, carrier, or excipient.

37 Claims, 1 Drawing Sheet

MILK PROTEIN MIXTURE FOR PROMOTING GROWTH OF ANIMAL CELLS OR TREATING WOUNDS AND METHOD OF MAKING AND METHODS EMPLOYING THE MIXTURE

This invention relates to the growth of animal cells in a cell culture composition. More specifically it relates to the provision of a cell culture composition including a cheese whey extract composition.

Animal cells are grown in culture to provide a number of pharmaceutical, diagnostic and veterinary products including human vaccines, lymphokines, hormones, monoclonal antibodies, Other pharmaceutically active protein products, and veterinary hormones and for research and development and diagnostic purposes.

The growth of animal cells requires a defined isotonic medium that contains salts, nutrients, lipid precursors, nucleic acid precursors, vitamins and amino acids that are formulated to mimic the medium that would normally bathe those cells in vivo. Examples in common use include Eagle's Minimal Essential Medium, Dulbecco's modified Eagle's Minimal Essential Medium (DMEM), Medium 199, RPMI 1640 medium and Ham's F12 Medium. However, virtually no animal cells will grow in such a medium, but require the co-addition of serum. Fetal bovine serum is frequently used as it is more effective than serum obtained from post-natal animals and it contains only minimal concentrations of immunoglobulins which otherwise could have undesirable effects.

The supply of fetal bovine serum is limited by the number of pregnant cows slaughtered. It also has undesirable lot-to-lot variations and may include toxins. Particular concern surrounds its use for the eventual production of recombinant proteins and other pharmaceuticals for human use because the serum may also contain viruses that are harmful to humans and may be carried through a purification protocol that yields the desirable product. Principally for these reasons, extensive efforts have been directed towards the replacement of serum by pure ingredients. Examples of such ingredients are growth factors, hormones and cell attachment factors. Unfortunately, the requirements of each cell type being grown are different and are difficult to establish. Frequently it has not proved possible to achieve equivalent growth properties or equivalent yields of cell products with "serum-free" media as can be obtained with medium containing fetal bovine serum.

The limited availability of fetal bovine serum, its lot-to-lot variability, its resultant considerable cost as well as the deficiencies of "serum-free" media described above have prompted the investigation of other biological fluids as potential replacements in cell culture media. Some progress has been reported in the prior art with bovine milk and bovine colostrum as evidenced by the following selected reports: M. Klagsbrun: "Human milk stimulates DNA synthesis and cell proliferation in cultured fibroblasts" (Proc. Natl. Acad. Sci. USA 75, 5057, 1978); M. Klagsbrun & J. Neumann: "The serum-free growth of Balb/c 3T3 cells in medium supplemented with bovine colostrum" (J. Supramol. Struct. 11, 349, 1979).

The prior art also includes U.S. Pat. No. 4,440,860 to M. Klagsbrun which describes "compositions and methods for promoting cell growth featuring, in one aspect, cell culture media containing milk or colostrum and fibronectin; fibronectin is preferably pre-coated onto the culture substrate" and Japan Patent JP 59166879 to Morinaga "A culture medium for cell incubation—containing milk or milk components". Ultrafiltrates of milk whey have also been used to support the growth of cultured cells, as in European Patent 86401911.2 to G. Linden et al. "Fractions de lait, Procedee d'obtention de ces fractions et milleux de culturo cellulaires renfermant ces fractions" and O. Damerdji et al. "Utilization of whey fractions as a substitute for fetal calf serum in culture media" (Biotech. Tech. 2, 235, 1988).

Despite this progress, a successful alternative to fetal bovine serum is yet to be located.

It is accordingly an object of the present invention to overcome, or at least alleviate one or more of the difficulties or deficiencies related to the prior art.

Accordingly in a first aspect of the present invention there is provided a milk product extract composition including a plurality of cell growth stimulating factors, extracted from a milk product, in a concentrated form; said factors having basic to approximately neutral isoelectric points.

By the term "milk product" we mean an extract from a human or animal milk product in which the salt and/or main protein constituents thereof are reduced or eliminated. Examples of milk extract include cheese whey extracts, skim milk extract and acid (casein) whey.

Figure 1A:
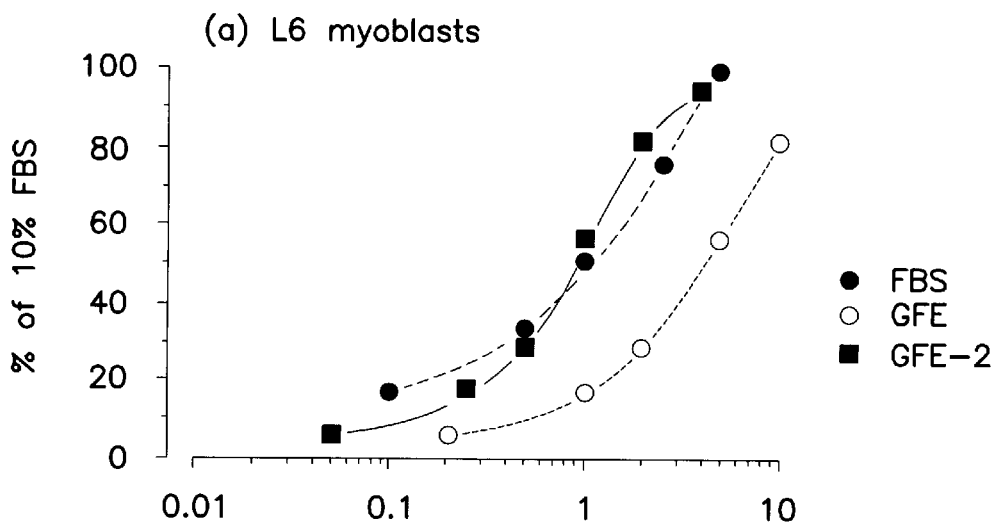
FIG. 1 illustrates the effect of fetal bovine serum, GFE and GFE-2 on the proliferation of T6 myoblasts, Balb C/3T3 cells, and SF1972 cells.

The present invention will be more fully described with reference to the preferred cheese whey extracts. However, this is illustrative only and should not be taken as a restriction on the generality of the invention.

Preferably the milk product extract composition is a cheese whey extract composition.

The cheese whey extract composition may be formed from cheese whey wherein the salt and/or main protein constituents thereof are reduced or eliminated.

The milk product extract composition may include less than approximately 1% w/w salt, based on the total weight of the composition. The milk product extract may include less than approximately 0.5% w/w casein, alpha lactalbumin, beta lactoglobulin, immunoglobulin or albumin, based on the total weight of the composition.

The milk product extract composition according to this aspect of the present invention may be utilized in the promotion of cell growth and proliferation in vitro as discussed below. The milk product extract composition may be utilized in stimulation of surface wound repair in vivo, in mammals as discussed below.

Surprisingly, the milk product extract composition may support the growth of animal cells at lower protein concentrations than achieved with fetal bovine serum, yet with an efficacy comparable to fetal bovine serum for several cell types.

Alternatively, the cheese whey extract may be used as a supplement to media containing low concentrations of fetal bovine serum in order to achieve better growth rates of cultured cells and to conserve the use of fetal bovine serum.

Cheese whey is a by-product of the cheese industry that has had essentially all the fat and casein removed during cheese manufacture. At the present state of the art cheese whey is essentially valueless, and indeed it may represent a net cost to the industry since it is a potential pollutant.

Cheese whey for example is a low protein, high salt product available in tonne amounts from cheese manufacture. The main protein constituents present in cheese whey are alpha lactalbumin (αLA) and beta lactoglobulin (βLG), which usually account for more than 90% of the proteins present. Significant amounts of serum albumin, immunoglobulins and residual casein may be present. All of these proteins have acidic isoelectric points. In contrast, the main protein factors that stimulate the growth of animal cells have basic isoelectric points. Examples include the growth factors basic FGF, IGF-I, des(l-3)IGF-I and PDGF. It is postulated that the extraction of the basic factors present in milk products such as cheese whey in the virtual absence of the otherwise abundant acidic proteins may account for the surprising efficacy of the milk product extract composition.

Accordingly in a further aspect of the present invention, there is provided a method for preparing a milk product extract composition including a plurality of cell growth stimulating factors, extracted from a milk product in a concentrated form; said factors having basic to approximately neutral isoelectric points, which method includes providing a source of milk product;

a cationic exchange resin; and a buffer solution;

contacting the milk product with the cation exchange resin such that the more basic components of the milk product are absorbed thereon;

eluting the cationic exchange resin with the buffer solution; and filtering the eluate to remove salt therefrom.

The desorption of the basic proteins from the ion exchange resin leads to a preparation enriched in cell growth stimulating factors. The eluate may be concentrated and filtered utilizing any suitable technique. The eluate may be concentrated for example by conventional ultrafiltration methods or other procedures to yield a mixture of proteins which supports the growth of animal cells when added to protein-free media such as DMEM.

The source of milk product may be a milk product filtrate substantially free of insoluble material. Accordingly the preparation method may include the preliminary step of filtering the milk product to remove insoluble materials therefrom.

The milk product may be filtered through a suitable sieve. The milk product may be filtered through a hollow fiber cartridge of defined porosity.

The cationic exchange resin may be of any suitable type. A Sepharose—based cation exchange gel may be used. The contacting step may be conducted at neutral to basic pH. The contacting step may be conducted at a pH of approximately 6.5 to 8.0.

The cationic exchange resin may be equilibrated with a suitable buffer at a pH of approximately 6.5 to 8.0. An aqueous sodium citrate buffer may be used. The elution steps may be conducted utilizing a suitable eluate. A salt solution may be used. A buffered saline solution may be used.

Thus in a preferred form of this aspect of the present invention the method of preparing a milk product extract composition may include treating the milk product sequentially by:

subjecting the milk product to a filtration step, to remove insoluble materials therefrom;

adjusting the pH of the filtrate to between approximately 6.5 and 8.0;

contacting the filtrate with a cationic exchange resin;

eluting from the cation exchange resin at high ionic strength and high pH with a suitable buffer solution; and subjecting the eluate to a concentration step and diafiltration step to remove salt therefrom.

Alternatively, the elution from the cation exchange resin is achieved at high ionic strength but without adjusting pH, such that the cell growth stimulating factors are recovered.

In this embodiment the cell growth stimulating factors are eluted with less extraneous protein.

In a further aspect of the isolation of a suitable extract from cheese whey, the eluant may be treated at high temperature and centrifuged. This modification removes additional protein. Accordingly, the method may further include subjecting the eluant to a heat treatment to reduce the content of extraneous protein.

The milk product extract composition may be sterilized and optionally freeze-dried for storage. The freeze-dried material may be dissolved in sterile saline for addition to cells in culture.

In a further aspect of the present invention there is provided a cell culture composition including an effective amount of a milk product extract composition including a plurality of cell growth stimulating factors, extracted from the milk product, in a concentrated form; said factors having basic to approximately neutral isoelectric points; and a culture medium.

The culture medium may be a substantially protein-free isotonic culture medium. The substantially protein-free isotonic culture medium may be Dulbecco's-modified Eagle's minimal Essential Medium (DMEM).

It has been found that an approximately equivalent growth rate of human skin fibroblasts to that achieved with 5% fetal bovine serum may be achieved with approximately 20 µg of cell growth stimulating factors extracted from cheese whey according to the preferred aspect of the present invention per 100 µl of medium.

Alternatively, a small, but effective amount of fetal bovine serum may be utilized as the culture medium. It has been found that the addition of approximately 25 µg of cell growth stimulating factors per 100 µl of medium containing approximately 2% fetal bovine serum will increase the growth rate of Balb C/3T3 cells to that rate otherwise achieved with 10% fetal bovine serum.

Other additions may be made to the medium, depending on the cell type, including growth factors, attachment factors or low amounts of serum.

In a preferred form, the present invention provides a cell culture composition, as described above, wherein the milk product extract is present in media at a protein concentration of approximately 10 to 20,000 micrograms per ml, preferably 100 to 2,000 micrograms per ml.

Accordingly in a still further aspect of the present invention there is provided a method for culturing cells which method includes providing a source of animal cells; and a cell culture composition including an effective amount of a milk product extract composition including a plurality of cell growth stimulating factors, extracted from the milk product, in a concentrated form; said factors having basic to approximately neutral isoelectric points; and a substantially protein-free isotonic culture medium; and culturing the cells in the cell culture composition for a time sufficient, and at a temperature sufficient to achieve a predetermined cell concentration.

The cell culture method may be conducted at ambient temperature or above. A temperature in the range of approximately 35° to 40° C. may be used. The cell culture process may be conducted in an incubator, for example a humidified incubator.

The cell culture method may be conducted on any suitable surface or in suspension. Tissue culture plates may be used.

The cell culture method may continue for a period of approximately 1 to 5 days depending on the cell concentration desired.

Although the method in particular applies to the growth of animal cells in vitro, it can also be applied to animals, including humans, that have surface wounds.

Accordingly, in a further aspect, the present invention provides a pharmaceutical or veterinary composition for the treatment of surface wounds, which composition includes:

an effective amount of a milk product extract composition including a plurality of cell growth promoting factors, extracted from the milk product in a concentrated form; said factors having basic to approximately neutral isoelectric points; and a pharmaceutically or veterinarily-acceptable diluent, carrier or excipient therefor.

The pharmaceutical or veterinary composition may further include an effective amount of at least one active ingredient.

The at least one active ingredient may be selected from antibiotics, antiseptics, other growth promotants, anaesthetics, and the like, and mixtures thereof.

The pharmaceutical or veterinary composition may be adapted for administration in any suitable manner. The composition may be adapted for internal or topical administration. The composition may be in an oral, injectable or topical form. Topical administration is preferred. The composition may take the form of a wash, lotion, cream, ointment or gel.

There are no limitations to the type of surface wound that may be treated, and these include, but are not limited to burns, ulcers, lacerations and penetrations.

Accordingly, in a further aspect of the present invention there is provided a method of treating surface wounds in animals, including humans, which method includes administering to the patient to be treated an effective amount of a pharmaceutical or veterinary composition, which composition includes an effective amount of a milk product extract composition including a plurality of cell growth promoting factors, extracted from a milk product in a concentrated form; said factors having basic to approximately neutral isoelectric points; and a pharmaceutically or veterinarily-acceptable diluent, carrier or excipient therefor.

The method can also be applied to animals, including humans, that have gastrointestinal injuries, diseases or ulcers.

Accordingly, in a further aspect, the present invention provides a pharmaceutical or veterinary composition for the treatment of gastrointestinal injuries, diseases or ulcers, which composition includes:

an effective amount of a milk product extract composition including a plurality of cell growth promoting factors, extracted from a milk product in a concentrated form; said factors having basic to approximately neutral isoelectric points; and a pharmaceutically or veterinarily-acceptable diluent, carrier or excipient therefor.

There are no limitations to the type of gastrointestinal injury, disease or ulcer that may be treated.

Accordingly, in a still further aspect of the present invention, there is provided a method for the treatment of gastrointestinal injuries, diseases or ulcers, which method includes administering to the patient to be treated an effective amount of a pharmaceutical or veterinary composition, which composition includes an effective amount of a milk product extract composition including cell growth promoting factors, extracted from a milk product in a concentrated form and having a basic to approximately neutral isoelectric point; and a pharmaceutically or veterinarily acceptable diluent, carrier or excipient therefor.

The present invention will now be more fully described with repsect to the following examples. It should be understood, however, that the description following is illustrative only, and should not be taken in any way as a restriction on the generality of the invention described above.

EXAMPLE 1

Preparation of a Fraction From Cheese Whey (GFE) That is Enriched in Growth-Promoting Activity Pasteurized whey obtained as an end product of cheese manufacture was filtered through a 10 micron screen and a 0.2 micron Sartorius Microsart Sartocon II module to remove solids. The ultrafiltrate was adjusted to pH 6.5 and applied to a column of S-Sepharose Fast Flow S cation exchange resin (Pharmacia) that had been equilibrated with 50 mM sodium citrate buffer at pH 6.5. After washing the column with the same buffer the absorbed material was eluted by a solution of 1M NaCl containing 0.25M $NH_4OH$. This eluate was diafiltered against water until the conductivity reached 0 $\mu s$ and then concentrated by ultrafiltration; both processes using a 3 KDa-excluding membrane. The resultant preparation was freeze-dried to produce the "GFE" product.

A preparation from 30 liters of cheese whey containing 18 g protein yielded a GFE extract containing 2.66 g protein.

EXAMPLE 2

Preparation of a Fraction From Cheese Whey That is Enriched in Growth-Promoting Activity and Depleted in Extraneous Protein Including Lactoferrin (GFE-2)

Pasteurized whey was filtered and applied to a column of S-Sepharose and the column washed as in Example 1. Elution was accomplished with a solution containing 0.4M NaCl added to 10 mM sodium citrate pH6.5. This GFE-2 was diafiltered against water, concentrated and freeze-dried as described in Example 1.

A preparation from 30 liters of cheese whey which contained 18 g protein yielded a GFE-2 extract containing 0.56 g protein.

EXAMPLE 3

Preparation of a Modified GFE-2 Fraction That is Also Depleted in Extraneous Protein Including Lactoperoxidase (GFE-3)

The freeze-dried GFE-2 (Example 2) was dissolved at a concentration of 25 mg/ml and heated at 80° C. for 2.5 min. The heated sample was cooled rapidly and centrifuged. The clear supernatant was passed through a 0.22 $\mu m$ filter before use. This solution contained 50% of the protein present in GFE-2 and approximately 10% lactoperoxidase.

EXAMPLE 4

Stimulation of the Growth of Cultured Cells by Cheese Whey Extracts (Examples 1,2) Compared With Fetal Bovine Serum Prior to addition to culture media, the freeze-dried powders (GFE, GFE-2) were first suspended in Dulbecco's Phosphate-buffered saline and sterilized by passage through a 0.22 $\mu m$ filter.

This example utilizes the cell lines L6 (rat myoblast), Balb C/3T3 (mouse fibroblast) and SF1972 (human diploid skin fibroblast).

Each cell line was subcultured on to 96-place tissue culture plates in Dulbecco-Modified Eagles's Minimal Essential Medium (DMEM) containing 5% fetal bovine serum and left in a 5% $CO_2$, 37° C., humidified incubator overnight to ensure attachment of the cells. Sterile techniques were used throughout. The plates were thoroughly washed in DMEM to remove any residual serum and the whey extract (GFE or GFE-2) or fetal bovine serum (FBS) added at the indicated concentrations. The total volume in each well was 0.1 ml at 37° C., 5% $CO_2$ and 100% humidity.

Figure 1B:
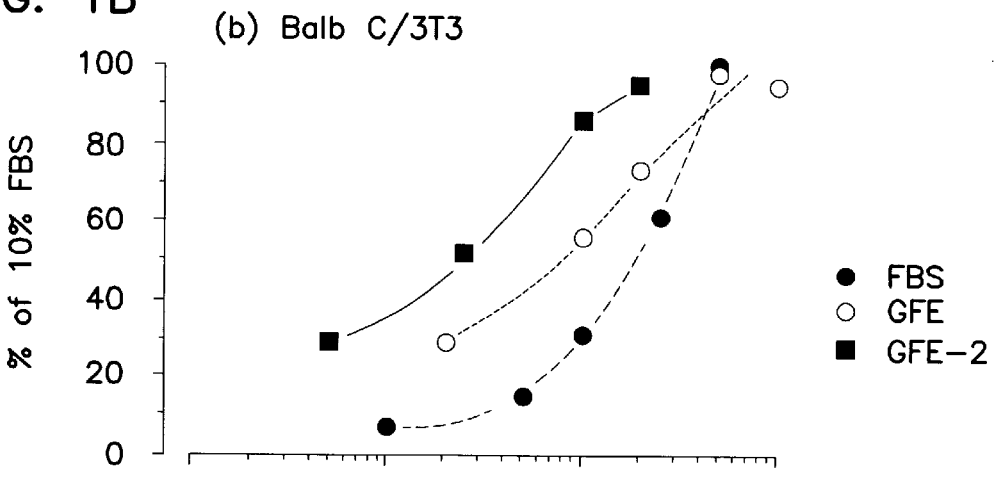
Figure 1C:
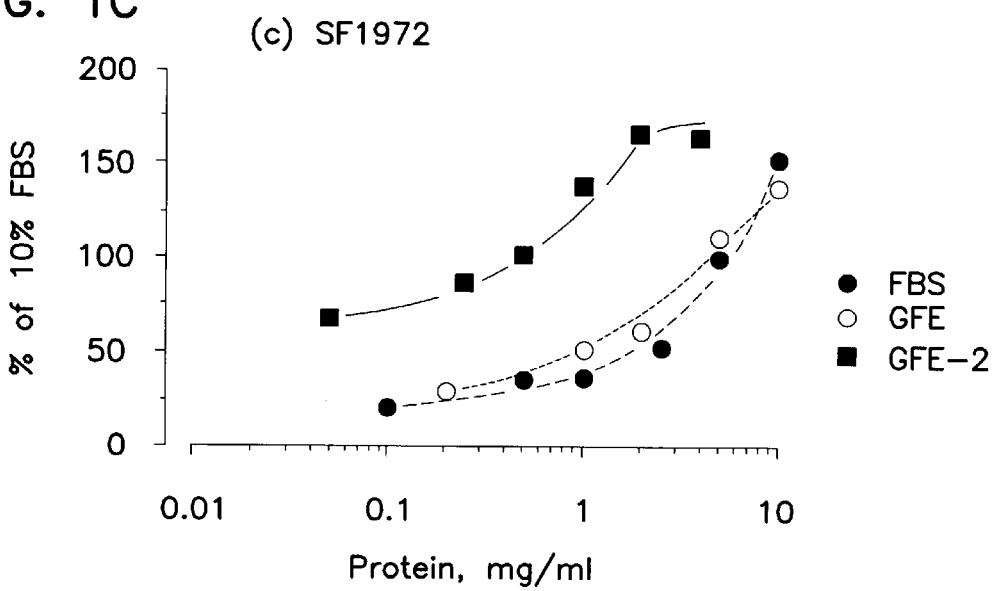

After a further 2 days the plates were washed, fixed and the cell numbers quantified using an automated methylene blue method (M. H. Oliver et al., J. Cell Sci. 92, 513, 1989). Growth is expressed as the percentage increase in absorbance units relative to the increse in absorbance produced by growing the cells in DMEM containing 5% fetal bovine serum (FIG. 1).

This example shows that in all three cell lines GFE and GFE-2 stimulate growth as well as fetal bovine serum. Moreover, in Balb C/3T3 and SF1972 cells GFE-2 is active at approximately one tenth the protein content as fetal bovine serum.

EXAMPLE 5

Stimulation of the Growth of Cultured Cells by Extracts of Cheese Whey Depleted in Extraneous Protein Including Lactoperoxidase (GFE-3. Example 3) Compared With GFE-2 (Example2)

The experimental details were exactly as described in Example 4 except that the data are expressed as the protein content ($\mu$g/100 $\mu$l well) that achieved the same growth response as was achieved with 5% fetal bovine serum (see Table 1).

TABLE 1

Growth of Cells in the presence of GFE-2 or GFE-3

| Cell Type | Extract | Concentration ($\mu$g/100 $\mu$l) achieving growth equivalent to 5% fetal bovine serum |
|---|---|---|
| L6 | GFE-2 | 100 |
|  | GFE-3 | 63 |
| Balb C/3T3 | GFE-2 | 15 |
|  | GFE-3 | 6 |
| SF1972 | GFE-2 | 8 |
|  | GFE-3 | 4 |

Clearly less GFE-3 is required to stimulate growth than GFE-2. Also since 5% fetal bovine serum has a protein content of 250 $\mu$g/100 $\mu$l, both GFE-2 and GFE-3 are very substantially more potent than 5% fetal bovine serum, especially for Balb C/3T3 cells and human skin fibroblasts (SF1972).

EXAMPLE 6

Growth Effects of Cultured Cells Produced by Supplementing Medium Containing 2% Fetal Bovine Serum With GFE-2 Extracts (Example 2)

The experimental details were exactly as described in Example 4 except that the human lung fibroblast line (HEL) replaced the human skin fibroblast line (SF1972). Data are expressed as absorbances achieved after growth of the cells for 2 days (see Table 2).

TABLE 2

Growth of Cells with GFE-2 added in the presence of 2% fetal bovine serum

| Fetal Bovine Serum (%) | GFE-2 ($\mu$g/100 $\mu$l) | Increases in absorbance | | |
|---|---|---|---|---|
| | | L6 cells | Balb C/3T3 cells | HEL cells |
| 2 | 0 | 0.618 | 0.126 | 65 |
| 5 | 0 | 0.998 | 0.270 | 10 |
| 10 | 0 | 1.309 | 0.502 | 0.345 |
| 2 | 5 | 1.010 | 0.294 | 0.322 |
| 2 | 25 | 1.108 | 0.585 | 0.388 |
| 2 | 50 | 1.157 | 0.698 | 0.389 |
| 2 | 100 | 1.370 | 0.799 | 0.374 |

This experiment demonstrates that low amounts of GFE-2 added to medium containing only 2% fetal bovine serum can increase the growth rate to that achieved with 10% fetal bovine serum. The approximate amount of GFE-2 required to achieve this growth enhancement was 100 $\mu$g/100 $\mu$l in L6 cells, 25 $\mu$g/100 $\mu$l in Balb C/3T3 cells and only 5 $\mu$g/100 $\mu$l in HEL cells. Such an enhancement represents a very substantial saving of fetal bovine serum.

Finally, it is to be understood that various other modifications and/or alterations may be made without departing from the spirit of the present invention as outlined herein.

We claim:

1. A composition for promoting growth of animal cells in culture, the composition consisting essentially of:
   (a) a milk protein mixture from a milk product selected from the group consisting of cheese whey, skim milk, and whey, the milk protein mixture comprising growth factors having a basic to approximately neutral isoelectric point, being enriched in growth promoting activity, and stimulating proliferation of rat myoblasts, the milk protein mixture being prepared by:
      filtering the milk product to remove insoluble material therefrom;
      adjusting the pH of the resulting ultrafiltrate to between approximately 6.5 and 8.0;
      equilibrating an agarose-based cation exchange resin with an equilibration buffer to provide a cation resin suitable for adsorbing basic protein;
      applying the pH adjusted ultrafiltrate to the equilibrated cation exchange resin;
      eluting the cation exchange resin with a buffer suitable for such eluting;
      filtering the eluate to reduce the salt content thereof;
      concentrating the filtered eluate to obtain the milk protein mixture enriched in growth promoting activity and stimulating proliferation of rat myoblasts; and
   (b) a liquid culture medium.

2. The milk protein mixture according to claim 1, wherein said milk product is cheese whey.

3. The composition according to claim 1, wherein said liquid culture medium is substantially protein free.

4. The composition according to claim 1, wherein said liquid culture medium further comprises fetal bovine serum.

5. The milk protein mixture according to claim 1, wherein the equilibration buffer is 50 mM sodium citrate at pH 6.5.

6. The milk protein mixture according to claim 5, wherein the eluting buffer comprises 1M NaCl containing 0.25M $NH_4OH$ or 0.4 NaCl added to 10 mM sodium citrate pH 6.5.

7. The milk protein mixture according to claim 6, wherein filtering comprises filtering against water until the conductivity approaches 0 $\mu$s.

8. The milk protein mixture according to claim 7, wherein concentrating comprises ultrafiltration using a 3 kD excluding membrane.

9. The composition according to claim 1, comprising a protein concentration of 10 to 20,000 micrograms per ml of culture medium.

10. A method for culturing animal cells including the steps of:
(a) providing animal cells;
(b) providing a composition according to claim 1; and
(c) culturing said animal cells for a time and at a temperature sufficient to promote cell growth.

11. The method according to claim 10, wherein the cells are cultured at a temperature in the range of 35° C. to 40° C. for a period of one to five days.

12. A milk protein mixture from a milk product selected from the group consisting of cheese whey, skim milk, and casein whey, the milk protein mixture comprising growth factors having a basic to approximately neutral isoelectric point, being enriched in growth promoting activity, and stimulating proliferation of rat myoblasts, the milk protein mixture comprising less than about 20 wt-% of milk protein present in the milk product; the milk protein mixture being prepared by:

filtering the milk product to remove insoluble material therefrom;
adjusting the pH of the resulting ultrafiltrate to between approximately 6.5 and 8.0;
equilibrating an agarose-based cation exchange resin with an equilibration buffer to provide a cation exchange resin suitable for absorbing basic protein;
applying the pH adjusted ultrafiltrate to the equilibrated cation exchange resin;
eluting the cation exchange resin with a buffer suitable for such eluting;
filtering the eluate to reduce the salt content thereof;
concentrating the filtered eluate to obtain the milk protein mixture enriched in growth promoting activity and stimulating proliferation of rat myoblasts.

13. The milk protein mixture according to claim 12, wherein said milk product is cheese whey.

14. The milk protein mixture according to claim 12, wherein the equilibration buffer is 50 mM sodium citrate at pH 6.5.

15. The milk protein mixture according to claim 12, wherein the eluting buffer comprises 1M NaCl containing 0.25M $NH_4OH$ or 0.4 NaCl added to 10 mM sodium citrate at pH 6.5.

16. The milk protein mixture according to claim 12, wherein filtering comprises filtering against water until the conductivity approaches 0 $\mu$s.

17. The milk protein mixture according to claim 12, wherein concentrating comprises ultrafiltration using a 3 kD excluding membrane.

18. A method for making a milk protein mixture from a milk product selected from the group consisting of cheese whey, skim milk, and acid casein whey, the milk protein mixture comprising growth factors having a basic to approximately neutral isoelectric point, being enriched in growth promoting activity, and stimulating proliferation of rat myoblasts, the milk protein mixture comprising less than about 20 wt-% of milk protein present in the milk product; the milk protein mixture being prepared by:

filtering the milk product to remove insoluble material therefrom;
adjusting the pH of the resulting ultrafiltrate to between approximately 6.5 and 8.0;
equilibrating an agarose-based cation exchange resin with an equilibration buffer to provide a cation exchange resin suitable for absorbing basic protein;
applying the pH adjusted ultrafiltrate to the equilibrated cation exchange resin;
eluting the cation exchange resin with a buffer suitable for such eluting;
filtering the eluate to reduce the salt content thereof;
concentrating the filtered eluate to obtain the milk protein mixture enriched in growth promoting activity and stimulating proliferation of rat myoblasts.

19. The method according to claim 18, wherein said milk product is cheese whey.

20. The method according to claim 18, wherein the equilibration buffer is 50 mM sodium citrate at pH 6.5.

21. The method according to claim 18, wherein the eluting buffer comprises 1M NaCl containing 0.25M $NH_4OH$ or 0.4 NaCl added to 10 mM sodium citrate at pH 6.5.

22. The method according to claim 18, wherein filtering comprises filtering against water until the conductivity approaches 0 $\mu$s.

23. The method according to claim 18, wherein concentrating comprises ultrafiltration using a 3 kD excluding membrane.

24. A composition for treatment of a surface wound or a gastrointestinal injury, disease, or ulcer, the composition consisting essentially of:
(a) a milk protein mixture from a milk product selected from the group consisting of cheese whey, skim milk, and acid casein whey, the milk protein mixture comprising growth factors having a basic to approximately neutral isoelectric point, being enriched in growth promoting activity, and stimulating proliferation of rat myoblasts, the milk protein mixture comprising less than about 20 wt-% of milk protein present in the milk product; the milk protein mixture being prepared by:
filtering the milk product to remove insoluble material therefrom;
adjusting the pH of the resulting ultrafiltrate to between approximately 6.5 and 8.0;
equilibrating an agarose-based cation exchange resin with an equilibration buffer to provide a cation exchange resin suitable for absorbing basic protein;
applying the pH adjusted ultrafiltrate to the equilibrated cation exchange resin;
eluting the cation exchange resin with a buffer suitable for such eluting;
filtering the eluate to reduce the salt content thereof;
concentrating the filtered eluate to obtain the milk protein mixture enriched in growth promoting activity and stimulating proliferation of rat myoblasts; and
(b) a pharmaceutically or veterinarily acceptable diluent, carrier, or excipient.

25. The composition according to claim 24 further consisting essentially of an effective amount of at least one antibiotic, antiseptic, anaesthetic, or mixture thereof.

26. The composition according to claim 24, wherein said milk product is cheese whey.

27. The composition according to claim 24, wherein the equilibration buffer is 50 mM sodium citrate at pH 6.5.

28. The composition according to claim 24, wherein the eluting buffer comprises 1M NaCl containing 0.25M $NH_4OH$ or 0.4 NaCl added to 10 mM sodium citrate pH 6.5.

29. The composition according to claim 24, wherein filtering comprises filtering against water until the conductivity approaches 0 µs.

30. The composition according to claim 24, wherein concentrating comprises ultrafiltration using a 3 kD excluding membrane.

31. A method of treating a surface wound or a gastrointestinal injury, disease, or ulcer, the method comprising the step of:
administering to a subject having a surface wound or a gastrointestinal injury, disease, or ulcer an effective amount of a composition consisting essentially of:
(a) a milk protein mixture from a milk product selected from the group consisting of cheese whey, skim milk, and acid casein whey, the milk protein mixture comprising growth factors having a basic to approximately neutral isoelectric point, being enriched in growth promoting activity, and stimulating proliferation of rat myoblasts, the milk protein mixture comprising less than about 20 wt-% of milk protein present in the milk product; the milk protein mixture being prepared by:
filtering the milk product to remove insoluble material therefrom;
adjusting the pH of the resulting ultrafiltrate to between approximately 6.5 and 8.0;
equilibrating an agarose-based cation exchange resin with an equilibration buffer to provide a cation exchange resin suitable for absorbing basic protein;
applying the pH adjusted ultrafiltrate to the equilibrated cation exchange resin;
eluting the cation exchange resin with a buffer suitable for such eluting;
filtering the eluate to reduce the salt content thereof;
concentrating the filtered eluate to obtain the milk protein mixture enriched in growth promoting activity and stimulating proliferation of rat myoblasts; and
(b) a pharmaceutically or veterinarily acceptable diluent, carrier, or excipient.

32. The method according to claim 31, wherein the composition further consists essentially of an effective amount of at least one antibiotic, antiseptic, anaesthetic, or mixture thereof.

33. The method according to claim 31, wherein said milk product is cheese whey.

34. The method according to claim 31, wherein the equilibration buffer is 50 mM sodium citrate at pH 6.5.

35. The method according to claim 31, wherein the eluting buffer comprises 1M NaCl containing 0.25M $NH_4OH$ or 0.4 NaCl added to 10 mM sodium citrate pH 6.5.

36. The method according to claim 31, wherein filtering comprises filtering against water until the conductivity approaches 0 µs.

37. The method according to claim 31, wherein concentrating comprises ultrafiltration using a 3 kD excluding membrane.

* * * * *

UNITED STATES PATENT AND TRADEMARK OFFICE
CERTIFICATE OF CORRECTION

PATENT NO. : 5,866,418

DATED : FEBRUARY 2, 1999

INVENTOR(S) : BALLARD ET AL.

It is certified that error appears in the above-identified patent and that said Letters Patent is hereby corrected as shown below:

Col. 9, line 32, claim 12: "absorbing" should read --adsorbing--

Col. 10, line 5, claim 18: "absorbing" should read --adsorbing--

Col. 10, line 46, claim 24: "absorbing" should read --adsorbing--

Col. 11, line 28, claim 31: "absorbing" should read --adsorbing--

Signed and Sealed this

Eighth Day of February, 2000

Attest:

Q. TODD DICKINSON

*Attesting Officer*          *Commissioner of Patents and Trademarks*